United States Patent

Watari et al.

[11] Patent Number: 6,004,258
[45] Date of Patent: Dec. 21, 1999

[54] INTRAAORTIC BALLOON CATHETER WITH BLOOD FEED PASSAGE FORMED THEREIN FOR ASSISTING CIRCULATION

[75] Inventors: Masanobu Watari; Shintaro Fukunaga; Taijiro Sueda; Yuichiro Matsuura, all of Hiroshima, Japan

[73] Assignee: President of Hiroshima University, Higashihiroshima, Japan

[21] Appl. No.: 09/085,837

[22] Filed: May 28, 1998

[30] Foreign Application Priority Data

Jun. 9, 1997 [JP] Japan .................................. 9-150563

[51] Int. Cl.⁶ .................................................. A61M 29/02
[52] U.S. Cl. ............................................................ 600/18
[58] Field of Search ............................... 600/18; 604/96, 604/102

[56] References Cited

U.S. PATENT DOCUMENTS

| | | | |
|---|---|---|---|
| 4,648,384 | 3/1987 | Schmukler | 600/18 |
| 5,024,668 | 6/1991 | Peters et al. | 600/18 |
| 5,195,942 | 3/1993 | Weil et al. | 600/18 |
| 5,308,319 | 5/1994 | Ide et al. | 600/18 |
| 5,413,558 | 5/1995 | Paradis | 600/18 |
| 5,755,687 | 5/1998 | Donlon | 600/18 |

OTHER PUBLICATIONS

Masanobu Watari, et al., "An Aortic Balloon Catheter Incorporating A Conduit for Percutaneous Cardiopulmonary Support," Artif Organs, vol. 22, No. 2, (Feb. 1998), pp. 148–150.

Official Journal of the International Society for Artificial Organs and the International Faculty for Artificial Organs, vol. 21, No. 6, (Jun. 1997), p. 509.

*Primary Examiner*—William E. Kamm
*Assistant Examiner*—George R. Evanisko
*Attorney, Agent, or Firm*—Oblon, Spivak, McClelland, Maier & Neustadt, P.C.

[57] ABSTRACT

When both the IABP and the PCPS are used, they exhibit an excellent circulation assisting effect. In this case, however, sequela such as hypoxic encephalopathy may well occur after the heart failure is remedied. The invention provides an intraaortic balloon catheter capable of preventing such sequela. The balloon catheter of the invention includes a catheter main body part which is to be inserted into an aorta, and a balloon section formed on an outer peripheral portion of the catheter main body, to be inserted into the aorta together with the main body, and to be expandable and contractible in the aorta under the control of the IABP. An end portion of the catheter main body functions as an introductory portion of the catheter, and has a blood feed hole formed therein for introducing, into an artery such as the aortic arch, arterial blood of high oxygen concentration fed from a circulation assisting unit such as the PCPS. The catheter main body has a blood feed passage communicating, at one end thereof, with the blood feed hole which leads to the aorta, and communicating, at the other end thereof, with a PCPS connection port. The blood feed passage is used for sending the arterial blood of high oxygen concentration to the aorta via the blood feed hole.

3 Claims, 1 Drawing Sheet

INTRAAORTIC BALLOON CATHETER WITH BLOOD FEED PASSAGE FORMED THEREIN FOR ASSISTING CIRCULATION

BACKGROUND OF THE INVENTION

1. Field of the Invention

This invention relates to a blood circulation assisting apparatus, and more particularly to an intraaortic balloon catheter with a blood feed passage formed therein for assisting blood circulation.

2. Description of Related Art

As a circulation assisting method for treating cardiogenic shock due to acute cardiac infarction, artificial cardiopulmonary withdrawal, a low output failure symptom after open heart surgery, and various types of heart failure appearing in emergency medical care, intraaortic balloon pumping (hereinafter referred to as "IABP") is generally used, in order to reduce afterloads on the heart and increase the amount of blood flowing through the coronaria to thereby restore the cardio function. Actually, however, there are many serious cases in which cardiac function cannot easily be restored by simply using the IABP. Recently, improved medical care results have been obtained in such serious cases, using both the IABP and a percutaneous cardiopulmonary support (hereinafter referred to as "PCPS). The PCPS is a simple cardiopulmonary assisting unit which comprises a centrifugal pump, an artificial lung, a blood intake passage and a blood feed passage. In this unit, the blood pulled by the blood intake passage is subjected to gas exchange, and then guided to the blood feed passage.

Although the use of both the IABP and the PCPS exhibits an excellent circulation assisting effect, it is disadvantageous in light of long-term prognosis, since it may well cause sequela such as hypoxic encephalopathy after the heart failure is remedied. In the case of using the conventional femoral arterial blood feeding method, the blood into which oxygen is sufficiently introduced by the PCPS is hard to circulate through the brain. This difficulty is considered the reason why the hypoxic encephalopathy cannot be eased.

BRIEF SUMMARY OF THE INVENTION

The present invention has been developed in light of occurrence of hypoxic encephalopathy in conventional medical care, and aims to provide an intraaortic balloon catheter capable of preventing sequela such as hypoxic encephalopathy.

The circulating assisting method using both the IABP and the PCPS exhibits an excellent circulation assisting effect. In light of brain protection, however, the method has not yet shown any satisfactory hypoxic encephalopathy preventing results.

The invention provides an apparatus for effectively circulating, through the brain, blood into which a sufficient amount of oxygen has been added by the PCPS. To this end, the invention provides an intraaortic balloon catheter which contains a blood feed passage to be connected to a circulation assisting unit such as the PCPS, and has a blood feed hole formed in the tip of the balloon section of the catheter. When both the IABP and the PCPS are used, the single catheter of the invention can simultaneously function as the IABP catheter and the blood feed passage of the PCPS, thereby enabling blood, into which oxygen is sufficiently added by an artificial lung, to be supplied into the aortic arch, and hence enabling arterial blood of high oxygen concentration to be circulated through the brain. As a result, the invention can exhibit an excellent brain protection effect. In addition, the invention provides an apparatus capable of causing blood of sufficient oxygen concentration to flow through the coronary artery, thereby further improving the restoration of the cardiac function.

To attain these objects, the invention provides a balloon catheter comprising a catheter main body and a balloon section formed on an outer peripheral portion of the catheter main body and to be inserted into an aorta, the balloon section expandable and contractible in the aorta, wherein the catheter main body includes a blood feed hole formed in an end portion thereof, a blood feed passage extending along an axis of the main body and communicating, at one end thereof, with the blood feed hole, and a gas feed/intake passage extending along the axis of the main body and communicating, at one end thereof, with the balloon section to introduce gas into the balloon section and to pull gas therefrom to thereby expand and contract the balloon section.

Preferably, the blood feed passage communicates, at the other end thereof, with a PCPS connection port, and the gas feed/intake passage communicates, at the other end thereof, with an IABP-driving-unit connection port. More preferably, the blood feed passage has a one-way valve. Also preferably, the catheter main body has a side tube, and the blood feed passage also extends into the side tube. Yet preferably, the blood feed passage and the gas feed/intake passage extend concentric or parallel. The balloon section may be located adjacent to the blood feed hole.

Additional objects and advantages of the invention will be set forth in the description which follows, and in part will be obvious from the description, or may be learned by practice of the invention. The objects and advantages of the invention may be realized and obtained by the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

The invention will be described with reference to the following drawings.

DETAILED DESCRIPTION OF THE INVENTION

When a circulation assisting method using both the IABP and the PCPS is carried out to treat a cardiogenic shock due to acute cardiac infarction, artificial cardiopulmonary withdrawal, a low output failure symptom after open heart surgery, and various types of heart failure appearing in emergency medical care, it is important to keep blood circulation in the brain in a good condition in view of the protection of the brain while performing the IABP. A catheter according to the invention enables arterial blood, into which a sufficient amount of oxygen has been added by the PCPS, to be supplied to the aortic arch, thereby enabling excellent brain protection. A similar effect can be obtained in the coronary circulation, too, which contributes to the restoration of the cardiac function.

The preferred embodiment of the invention, which is useful in explaining the principle of the invention, will be described in detail with reference to the drawings. This embodiment, however, does not limit the scope of the invention.

Figure 1:
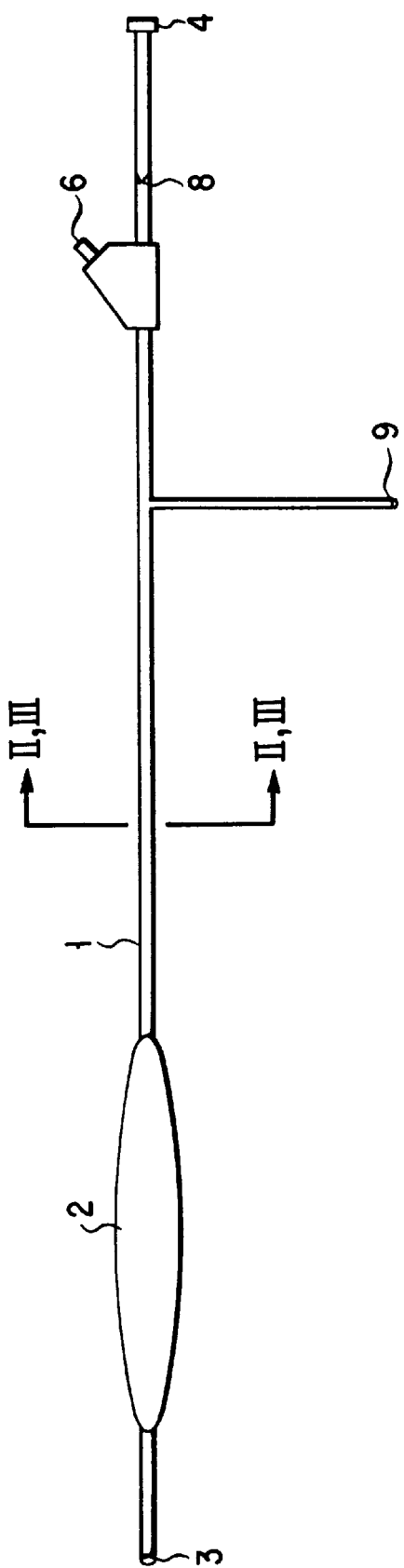
FIG. 1 is a view, showing a balloon catheter according to the invention.

FIG. 1 shows a balloon catheter according to the invention. Although the catheter has a basic structure similar to the usual IABP catheter, it is characterized by incorporating a blood feed passage within it, and is constructed as below.

Figure 3:
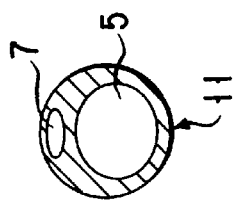
FIG. 3 is another sectional view of the main body of the catheter of FIG. 1.
Figure 2:
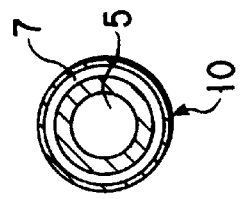
FIG. 2 is a cross-sectional view of the main body of the catheter of FIG. 1.

The balloon catheter of the embodiment comprises a catheter main body 1 having a portion thereof to be inserted into the aorta, and a balloon section 2 provided on an outer peripheral portion of the catheter main body 1 and to be inserted in the aorta together with the portion of the main body 1 such that it can expand and contract under the control of the IABP. An end portion of the catheter functions as a catheter guide, and has a blood feed hole 3 formed therein for guiding, into an artery such as the aortic arch, arterial blood of high oxygen concentration from a circulation assisting unit (not shown) such as the PCPS. To this end, the catheter main body 1 includes as shown in FIGS. 2 and 3, a blood feed passage 5 which has an end thereof connected to the blood feed hole 3 of FIG. 1 leading to the aorta and the other end connected to a PCPS connection port 4. The catheter main body 1 further includes in FIGS. 2 and 3 a gas feed/intake passage 7 which has an end thereof connected to the balloon section 2 and the other end connected to a connection port 6 in FIG. 1 to be led to an IABP driving unit (not shown). The passage 7 is used for introducing gas into the balloon section 2 and taking gas therefrom to make it expand and contract.

It is desirable to form the catheter main body 1 of a material with a certain flexibility, such as polyurethane, polyolefin, polyamide, polyclorinated biphenyl, polyethylene terephthalate, etc. Polyurethane is most preferable among them.

As described above, arterial blood of high oxygen concentration is fed from the PCPS into the aorta through the blood feed passage 5 and the blood feed hole 3. To feed a sufficient amount of blood with high oxygen concentration, it is desirable to make the blood feed passage 5 have as large an inner diameter as possible. Specifically, it is desirable to set the inner diameter of the passage 5 at 5 to 7 mm, in light of the structural relationship between the catheter main body 1 and the gas feed/intake passage 7 which are inserted into a blood vessel.

FIGS. 2 and 3 are cross-sectional views, taken along lines II, III—II, III of FIG. 1 and showing examples of the blood feed passage 5 and the gas feed/intake passage 7. A cross section 10 is shown of an example in which the passages 5 and 7 are formed concentric. Although in this case, the blood feed passage 5 occupies a center portion of the tube, the gas feed/intake passage 7 may be formed to occupy the center portion instead of the passage 5. A cross section 11 is shown of an example in which the passenges 5 and 7 are formed parallel to each other. In this case, the inner and outer tubes are fixed to each other by means of an appropriate supporting structure (not shown). It is a matter of course that the structure of the passages 5 and 7 of the invention is not limited to those mentioned.

The balloon section 2 is formed of, for example, a thin film with a thickness of about 100 to 200 μm. The material of the thin film needs to have a certain flexibility and hardness, be chemically stable inside the organism, and have a superior mechanical fatigue property. Therefore, the material is preferably polyethylene, polypropylene, silicone rubber, etc., and more preferably polyurethane. Further, it is desirable that the balloon section 2, when expanded, is 12 to 17 mm in outer diameter and 200 to 300 mm in length. The balloon section 2 is controlled by the IABP driving unit via the gas in the gas feed/intake passage 7, and expands and contracts in accordance with the beating of the heart. The catheter main body 1 and the balloon section 2 are adhered to each other by thermal fusion or an adhesive resin.

In FIG. 1, a one-way valve 8 for preventing reverse flow of blood can be provided across a predetermined portion of the blood feed passage 5, for example, in the vicinity of the PCPS connection port 4. This valve 8 can prevent reverse flow of blood from the artery toward the PCPS side, when, for example, simultaneous use of the PCPS and the IABP is switched to use of only the IABP. Although means for closing the blood feed passage 5 can be used instead of the one-way valve, the one-way valve 8 is more advantageous in that it requires no particular operation from the outside.

Moreover, in order to prevent ischemia in that portion of the femoral artery into which the catheter is inserted, and portions downstream of it, a side tube 9 which extends from the catheter main body 1 and is to be located outside the body of a patient may be inserted into, for example, the femoral artery so that blood from the inserted side tube 9 can circulate through the above-mentioned portions of the femoral artery. Since a smaller amount of blood is required for the side tube 9 than for the aortic arch, the flow rate of blood is controlled by setting the inner diameter of the side tube 9 smaller than that of the blood feed passage 5. For usual use, it is desirable to set the inner diameter of the side tube 9 at 1 to 1.5 mm when that of the blood feed passage 5 is 5 to 7 mm. The side tube 9 is made of the same material as the catheter main body 1, and adhered to the main body 1 by thermal fusion or an adhesive resin.

As described above, communication of the PCPS connection port 4 with the blood feed passage 5 of a circulation assisting unit such as the PCPS enables blood feed to the aortic arch from the blood feed hole 3 formed in one end of the catheter main body 1. In this case, the IABP can be performed simultaneously. The balloon catheter of the invention can execute the functions of both the conventional IABP catheter and PCPS blood feed passage.

The invention can supply theaortic arch with blood, into which a sufficient amount of oxygen is introduced through the artificial lung of the PCPS, thereby enabling circulation of arterial blood with high oxygen concentration and hence obtaining an excellent brain protection effect. In addition, the coronary artery is also supplied with blood of sufficient oxygen concentration, thereby further improving the restoration of the cardiac function.

Also, the invention enables reliable circulation of blood through that portion of the femoral artery into which the catheter is inserted, and portions downstream of it, using the side tube 9 attached to the catheter main body 1.

The balloon catheter of the invention can be used as both an IABP catheter and a PCPS blood feed passage, when, in particular, the circulation assisting method using both the IABP and the PCPS is executed for treating cardiogenic shock due to acute cardiac infarction, artificial cardiopulmonary withdrawal, a low output failure symptom after open heart surgery, and various types of heart failure appearing in emergency medical care. The catheter can be also used as an intraaortic balloon catheter which contains a circulation assisting blood feed passage and is used to restore the cardiopulmonary function and prevent hypoxic encephalopathy.

Naturally, the balloon catheter according to the above-described embodiment is just an example, and can be modified in various manners without departing from the technical scope of the invention.

The balloon catheter of the invention can provide the following advantages:

In the prior art, two catheters are necessary when both the IABP and the PCPS are used. On the other hand, the single balloon catheter of the invention can execute the functions of the two catheters. This advantage means that the influence of the medical instrument upon the organism is less than in the conventional case.

Since the balloon catheter of the invention can supply arterial blood of high oxygen concentration for brain circulation or coronary circulation while using the effects of the IABP and the PCPS, it can obtain an excellent brain protecting effect and cardiac function restoring effect. In other words, the catheter can directly supply the aortic arch, located near the brain and the heart, with arterial blood of high oxygen concentration fed from the PCPS, thereby further enhancing the brain protecting effect and cardiac function restoring effect.

The invention can be modified in various manners without departing from its spirit or gist. Thus, the above-described embodiment is just an example in all respects, and the invention is not limited to it. The scope of the invention is defined by the claims and not by the embodiment. Further, modifications or changes within the scope of the claims are included in the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A balloon catheter comprising:
   a catheter main body having a distal end portion and a proximal end portion; and
   an intra-aortic balloon section on an outer peripheral portion of the catheter main body, said balloon section being provided for insertion into the aorta and for expansion and contraction;
   wherein the catheter main body includes a blood feed hole on the distal end portion, a blood feed passage communicating with the blood feed hole and extending to the proximal end portion, a gas feed/intake passage communicating with the balloon section and extending to the proximal end portion, and a side tube, said blood feed passage also extending into the side tube, so that said balloon section is expanded by introducing gas via said gas feed/intake passage and contracted by pulling the gas via said gas feed/intake passage.

2. A balloon catheter according to claim 1, wherein said blood feed passage communicates, at the proximal end portion, with a percutaneous cardio pulmonary support connection port, and said gas feed/intake passage communicates, at the proximal end portion, with an intra-aortic balloon pumping driving unit connection port.

3. A balloon catheter according to claim 1,
   wherein said blood feed passage and said gas feed/intake passage extend concentric to each other in the catheter main body.

* * * * *